United States Patent [19]

Sauer et al.

[11] Patent Number: 4,524,208

[45] Date of Patent: Jun. 18, 1985

[54] PROCESS FOR THE PREPARATION OF LYSERGIC ACID ESTERS

[75] Inventors: Gerhard Sauer; Gregor Haffer, both of Berlin, Fed. Rep. of Germany

[73] Assignee: Schering Aktiengesellschaft, Berlin and Bergkamen, Fed. Rep. of Germany

[21] Appl. No.: 498,427

[22] Filed: May 26, 1983

[30] Foreign Application Priority Data

May 26, 1982 [DE] Fed. Rep. of Germany ....... 3220119

[51] Int. Cl.³ .................. C07D 457/04; C07D 457/06
[52] U.S. Cl. .................................................. 546/69
[58] Field of Search .......................................... 546/69

[56] References Cited

PUBLICATIONS

Berde and Schild, *Ergot Alkaloids and Related Compounds,* Springer-Verlag, New York, (1978), pp. 44, 45.
March, Jerry, *Advanced Organic Chemistry,* McGraw-Hill, New York, (1977), pp. 353–355, 367.
Noller, Carl, *Textbook of Organic Chemistry,* W. B. Saunders, Philadelphia, (1966), p. 234.
Weygand-Hilgetag, "Organisch-chemische Experimentierkunst", Leipzig 1970, p. 352.

A. Stoll and T. Petrzilka, Helv. Chim. Acta 36: 1125 (1953).

*Primary Examiner*—Donald G. Daus
*Assistant Examiner*—G. Hendricks
*Attorney, Agent, or Firm*—Millen & White

[57] ABSTRACT

A process for preparing lysergic acid esters of the formula

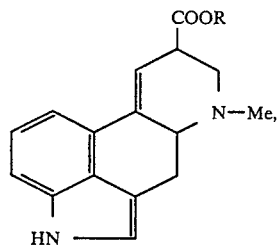

wherein
R is alkyl of up to 3 carbon atoms, comprises reacting corresponding lysergic acid or isolysergic acid amides with corresponding alcohols at temperatures of 0° to 65° C. for 2 to 30 hours in the presence of an acid at a pH value of 0–1.

10 Claims, No Drawings

PROCESS FOR THE PREPARATION OF LYSERGIC ACID ESTERS

BACKGROUND OF THE INVENTION

The present invention concerns a new method for preparing lysergic acid esters.

Lysergic acid esters are intermediates for the conventional production of pharmacologically active compounds and also of each other. Thus, the known lisuride hydrogen maleate (U.S. Pat. No. 3,251,846) can be prepared, via the intermediate stage of the azide, for example according to the process described by Zikan [V. Zikan et al., Coll. Czechoslov. Chem. Commun., 25:1922 (1960)], using any of the esters prepared by the process of this invention.

In general, an acid amide is prepared from the ester. However, it is also possible to conduct the inverse reaction, i.e., the conversion of an acid amide into the corresponding ester, in one step. For this purpose, the acid amide is dissolved in an alcohol and a strong acid is added thereto. In most cases, a high acid concentration is required, for example, by introducing hydrogen chloride for several hours. This reaction is ordinarily accomplished under boiling heat of the alcohol employed, in some cases even in a sealed tube (Weygand-Hilgetag, "Organisch-chemische Experimentierkunst" [Experimenting Art in Organic Chemistry] Leipzig 1970, p. 352).

On the other hand, it is also known that lysergic acid and its derivatives, especially the esters, are easily rearranged under strongly acidic conditions into entirely useless benz[c,d]indolines [A. Stoll and T. Petrzilka, Helv. Chim. Acta 36:1125 (1953)]. This poses a major problem in acid catalyzed reactions preparing or using such esters.

Alkaline saponification of lysergic acid amides likewise takes place under rather drastic conditions which 4-7N potassium hydroxide solution under heating. It does not yield pure lysergic acid which then would first have to be esterified in a second step (see DAS No. 2,610,859).

SUMMARY OF THE INVENTION

It is an object of the present invention to provide a process that produces the desired lysergic acid esters in the pure state in a high yield, e.g., typically at least about 80 molar % of theory.

It has now been found surprisingly that it is possible to convert lysergic acid and/or isolysergic acid amides, in the presence of an inorganic or organic acid, into the natural lysergic acid ester of 8$\beta$-configuration, in a smooth reaction, there additionally occurring in case of the isolysergic acid amide reactant, a surprising isomerization to the lysergic acid ester. The yields are practically quantitative.

Upon further study of the specification and appended claims, further objects and advantages of this invention will become apparent to those skilled in the art.

These objects have been achieved by providing a process for the preparation of lysergic acid esters of the formula

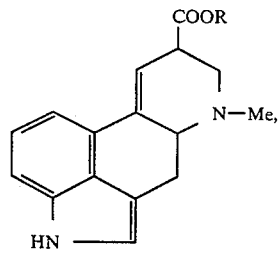

wherein
R is alkyl of up to 3 carbon atoms, comprising treating lysergic acid and/or isolysergic acid amides of the formula

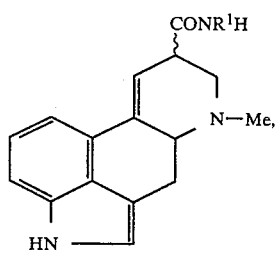

wherein
$R^1$ is hydrogen or lower alkyl of up to 4 carbon atoms, optionally substituted by an OH-group,
or a reaction compatible salt thereof with an acid,
with an alcohol of the formula ROH wherein R is alkyl of up to 3 carbon atoms, at temperatures of 0° to 65° C. for a period of 2 to 30 hours in the presence of an acid at a pH value of 0-1.

DETAILED DISCUSSION

In order to conduct the process, a lysergic acid amide or isolysergic acid amide or a mixture of both is dissolved in the corresponding alcohol, e.g., methanol, ethanol, n-propanol, or isopropanol. Generally, amounts of the amide relative to the alcohol are 1-10 parts by weight, i.e., usually an excess of alcohol is utilized. Suitable acids include for example sulfuric acid, hydrochloric acid, perchloric acid, p-toluenesulfonic acid, trifluoroacetic acid, trifluoromethanesulfonic acid, etc., or an acid in the form of an acidic ion exchange resin, e.g., sulfonic acids like $RSO_3H$, wherein R is the resin residue.

The acid is added to the alcohol solution in a quantity so that the pH value of the reaction solution is about 0-1. The reaction is carried out at 0° to the boiling temperature of the reaction mixture, generally up to 65° C.; suitably, the temperature range is 20°-55° C. The reaction temperature is maintained for a relatively long period of time. Depending on the acid concentration and reaction temperature the reaction period is 2 hours, usually at most 30 hours and, in the normal case, is completed after about 16 hours. Preferably, the reaction is conducted under anhydrous conditions.

Subsequently the reaction mixture is worked up by using known methods, such as washing, extraction, precipitation, crystallization, etc.

Suitable as starting materials in the reaction of this invention are all free and N-substituted lysergic acid amides and isolysergic acid amides of the formula

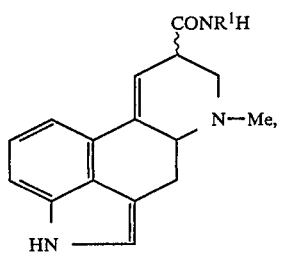

wherein $R^1$ is hydrogen or lower alkyl of up to 4 carbon atoms, which can optionally be substituted by an OH-group. Examples in this connection include lysergic acid amide, isolysergic acid amide, ergometrine, ergometrinine, etc. All of these starting materials are known or readily conventionally preparable.

Lower alkyl includes, for example, methyl, ethyl, n-propyl, isopropyl, butyl, etc., but especially methyl.

Acid salts of the amides can equivalently be used as starting materials, e.g., the hydrochloride, tartrate, hydrogen maleate, methane sulphonate and hydrogen phosphate.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A suspension is prepared from 5.0 g of isolysergic acid amide in 80 ml of anhydrous methanol; the mixture is cooled to about −50° C. and, under agitation, 40 ml of a 13N solution of hydrogen chloride in anhydrous methanol is added thereto. The clear solution is allowed to warm up to room temperature and further stirred overnight. The primary amount of the thus-formed ester hydrochloride is thus crystallized. By cooling in an ice bath and adding ethyl acetate, the crystallization is completed, and the precipitate is vacuum-filtered.

Yield: 5.2 g (84% of theory) of lysergic acid methyl ester, hydrochloride.

$[\alpha]_D = +94°$ (0.5% in methanol).

EXAMPLE 2

Starting with 5.0 g of lysergic acid amide, lysergic acid methyl ester is obtained as the hydrochloride in an 86% yield according to Example 1.

$[\alpha]_D = +94°$ (0.5% in methanol).

EXAMPLE 3

A mixture of 2.5 g of lysergic acid amide and 2.5 g of isolysergic acid amide in 500 ml of ethanol is heated with 100 g of p-toluenesulfonic acid for 4 hours to 50° C. Then half of the solvent is removed by distillation, the residue is poured into a mixture of 200 ml of concentrated ammonia and ice, and extracted with methylene chloride. The organic phase is dried with sodium sulfate and evaporated, thus obtaining after crystallization from ethanol 4.45 g (81% by theory) of lysergic acid methyl ester.

$[\alpha]_D = +68°$ (0.5% in chloroform).

EXAMPLE 4

A solution is prepared of 4.4 g of ergometrine maleate (10 millimoles) in 300 ml of methanol under nitrogen; 10 g of p-toluenesulfonic acid is added thereto, and the mixture is heated in a sealed flask overnight to 50° C. The solution is concentrated under vacuum, taken up in methylene chloride, and combined with concentrated ammonia solution until an alkaline reaction is obtained. After separating the phases and further extraction of the aqueous phase, the organic phases are dried with sodium sulfate and evaporated. The residue is crystallized from methylene chloride and diisopropyl ether.

Yield: 2.5 g (89% of theory) of lysergic acid methyl ester.

$[\alpha]_D = +84°$ (0.5% in chloroform).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a lysergic acid ester of the formula

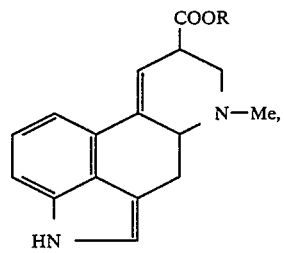

wherein

R is alkyl of up to 3 carbon atoms, comprising reacting a lysergic acid or isolysergic acid amide of the formula

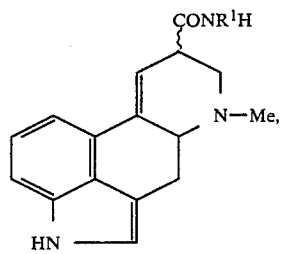

wherein $R^1$ is hydrogen or lower alkyl of up to 4 carbon atoms optionally substituted by an OH-group, or a reaction compatible salt thereof with an acid, with an alcohol of the formula ROH wherein R is alkyl of up to 3 carbon atoms, at a temperature of 0° to 65° C. for a period of 2 to 30 hours in the presence of an acid or an acidic ion exchange resin at a pH value of about 0–1.

2. A process of claim 1 wherein the starting material amide is a lysergic acid amide.

3. A process of claim 1 wherein the starting material amide is an isolysergic acid amide.

4. A process of claim 1 wherein the starting material amide is a mixture of lysergic and isolysergic acid amides.

5. A process of claim 1 wherein $R^1$ is methyl.

6. A process of claim 1 wherein the pH is provided by adding an acid.

7. A process of claim 1 wherein the pH is effectively provided by using an acidic ion exchange resin.

8. A process of claim 1 wherein the acid is HCl or p-toluenesulfonic acid.

9. A process of claim 1 wherein the reaction temperature is 20°–55° C.

10. A method of claim 1 wherein the reaction time is 16–2 hours.

* * * * *